(12) United States Patent
Vo-Dinh

(10) Patent No.: US 7,103,402 B2
(45) Date of Patent: Sep. 5, 2006

(54) ADVANCED SYNCHRONOUS LUMINESCENCE IMAGING FOR CHEMICAL AND MEDICAL DIAGNOSTICS

(75) Inventor: Tuan Vo-Dinh, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 274 days.

(21) Appl. No.: 10/677,703

(22) Filed: Oct. 2, 2003

(65) Prior Publication Data

US 2005/0075575 A1    Apr. 7, 2005

(51) Int. Cl.
    *A61B 5/00*    (2006.01)
(52) U.S. Cl. .............. 600/476; 600/473; 600/478; 606/15; 356/301
(58) Field of Classification Search ............ None
    See application file for complete search history.

(56) References Cited

U.S. PATENT DOCUMENTS

| | | | |
|---|---|---|---|
| 5,579,773 | A | 12/1996 | Vo-Dinh et al. |
| 5,599,717 | A | 2/1997 | Vo-Dinh |
| 5,938,617 | A | 8/1999 | Vo-Dinh |
| 6,208,887 | B1 * | 3/2001 | Clarke ............ 600/476 |
| 6,485,413 | B1 * | 11/2002 | Boppart et al. ........ 600/160 |

OTHER PUBLICATIONS

Vo-Dinh, T., "Multicomponent Analysis by Synchronous Luminescence Spectrometry", Anal. Chem., vol. 50, No. 3, pp. 396-401, (Mar. 1, 1978).

Vo-Dinh, T., "Synchronous Excitation Spectroscopy", Modern Fluorescence Spectroscopy, vol. 4, Ch. 5, Ed. by E.L. Wehry, (1981).

Vo-Dinh, T., "Synchronous Luminescence Spectroscopy: Methodolgy and Applicability", Appled Spectroscopy, vol. 36, No. 5, pp. 576-581, (Sep. 1, 1982).

Hueber, D.M., et al., "Fast Scanning Synchronous Luminescence Spectrometer Based on Acousto-Optic Tunable Filters", Applied Spectroscopy, vol. 49, No. 11, pp. 1624-1631(1995).

Vo-Dinh, T., et al., "Laser-Induced Differential Fluorescence for Cancer Diagnosis Without Biopsy", Applied Spectroscopy, vol. 51, No. 1, (1997).

Norton, S., et al., "Diffraction Tomographic Imaging With Photon Density Waves: An Explicit Solution", J. Opt. Soc. Am. A., vol. 15, No. 10, pp. 2670-2677, (Oct. 1998).

* cited by examiner

*Primary Examiner*—Brian L. Casler
*Assistant Examiner*—William Jung
(74) *Attorney, Agent, or Firm*—Akerman Senterfitt; Neil R. Jetter

(57) ABSTRACT

A diagnostic method and associated system includes the steps of exposing at least one sample location with excitation radiation through a single optical waveguide or a single optical waveguide bundle, wherein the sample emits emission radiation in response to the excitation radiation. The same single optical waveguide or the single optical waveguide bundle receives at least a portion of the emission radiation from the sample, thus providing co-registration of the excitation radiation and the emission radiation. The wavelength of the excitation radiation and emission radiation is synchronously scanned to produce a spectrum upon which an image can be formed. An increased emission signal is generated by the enhanced overlap of the excitation and emission focal volumes provided by co-registration of the excitation and emission signals thus increasing the sensitivity as well as decreasing the exposure time necessary to obtain an image.

25 Claims, 12 Drawing Sheets

FIG. 2A
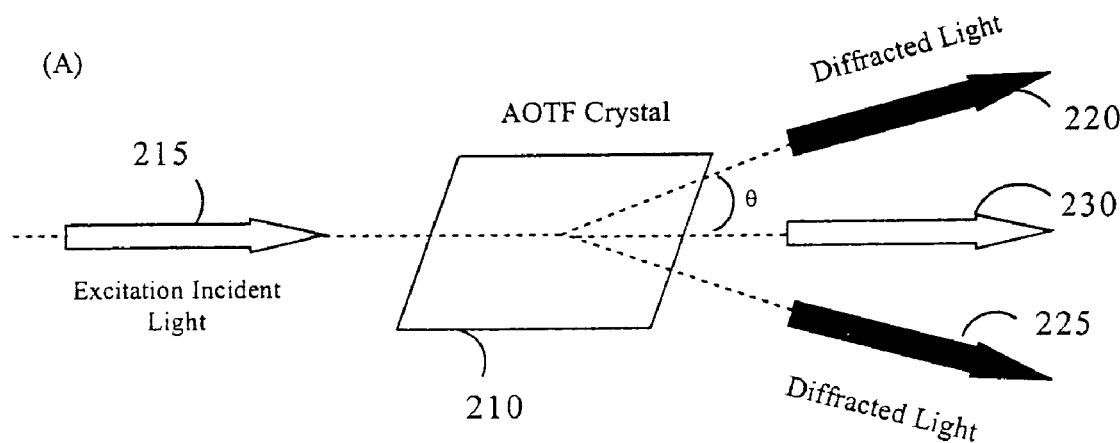
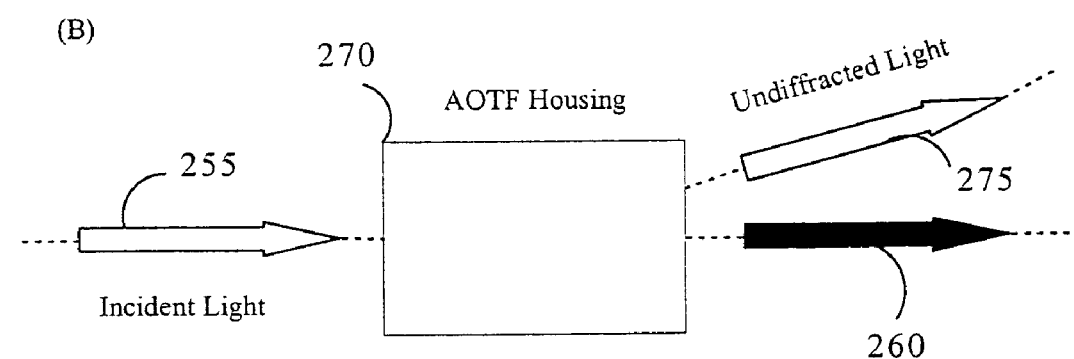
FIG. 2B
PRIOR ART

Reflection Image
($\lambda_{ex}$ = 488 nm $\lambda_{em}$ = 488 nm)

Fluorescence Image
($\lambda_{ex}$ = 488 nm $\lambda_{em}$ = 640 nm)

ADVANCED SYNCHRONOUS LUMINESCENCE IMAGING FOR CHEMICAL AND MEDICAL DIAGNOSTICS

STATEMENT REGARDING FEDERALLY SPONSORED RESEARCH OR DEVELOPMENT

The United States Government has rights in this invention pursuant to Contract AC05-00OR22725 between the United States Department of Energy and UT-Battelle, LLC.

CROSS-REFERENCE TO RELATED APPLICATIONS

Not applicable.

FIELD OF THE INVENTION

The invention relates to imaging, and more particularly to synchronous luminescence imaging for chemical and medical diagnostics.

BACKGROUND OF THE INVENTION

Although fixed-excitation laser-induced fluorescence (LIF) has been shown to be successful for differentiating normal from malignant tissues, this technique does not distinguish low-grade dysphasia from Barrett's mucosa without dysplasia. A limitation of the conventional fixed-excitation LIF technique results because it does not often provide the spectral specificity needed to provide clear "spectral fingerprints" of normal and dysplastic tissues mainly because the flourescence of tissue is a composite of fluorescence emissions from various tissue components. For example, tissue components generally include endogenous fluorophors such as aromatic amino acids (e.g., tryptophan, tyrosine, phenylalanine), structural matrix proteins (e.g., collagen, elastin), nicotiamide adenine dinucleotide (NADH), flavin adenine dinucleotide (FAD), porphyrins, Lipo-pigments (e.g., ceroids, lipofuscin), and other biological components. As a result, applied to tissue diagnostics LIF provides spectra that are poorly resolved and featureless because of spectral overlap between the emissions from individual tissue components. Thus, the laser used in LIF can only improve the sensitivity but cannot enhance the specificity (selectivity).

In addition to spectral specificity problems, current instrumentation for cancer and other tissue diagnostics have other serious limitations. One major limitation of the conventional fluorescence technique results from the use of a fixed-wavelength excitation source (e.g., a monochromatic laser). As noted above, each component in tissue (e.g., collagen, FAD, porphyrins, NADH, etc.) has specific absorption and emission spectra occurring in particular spectral ranges. When a single fixed laser line is used, it is difficult, if not impossible, to excite all the biological components under optimal conditions.

Synchronous luminescence (SL) methodology is an improved technology over LIF and provides a way to measure the luminescence signal and spectral fingerprints for rapid screening of complex chemical samples. The general theory of the SL method has been described previously in "Synchronous Excitation Spectroscopy," authored by the inventor of the present application T. Vo-Dinh, in Modern Fluorescence Spectroscopy, Chapter 5, Ed. by E. L. Wehry (Plenum Publ. Corp. 1981), which is incorporated herein by reference in its entirety. In contrast to SL, conventional luminescence spectroscopy uses either a fixed-wavelength excitation ($\lambda_{ex}$) to produce an emission spectrum or a fixed wavelength emission ($\lambda_{em}$) to record an excitation spectrum. With SL, the luminescence signal is recorded while both $\lambda_{em}$ and $\lambda_{ex}$ are simultaneously scanned. A constant wavelength interval is generally maintained between the excitation and the emission monochromators throughout the spectrum. As a result, the observed intensity $I_s$ of the synchronous signal can be written as a product of two functions as follows:

$$I_s(\lambda_{ex}, \lambda_{em}) = k\ c\ E_x(\lambda_{ex}) \cdot E_M(\lambda_{ex}) \qquad (1)$$

where:
k=a constant,
c=concentration of the analyte,
$E_x$=excitation function, and
$E_M$=emission function.

For a single molecular species the observed intensity $I_s$ is simplified often to a single peak, and the bandwidth is narrower than for the conventional emission spectrum. Since the SL spectrum of each component becomes sharper due to the band-narrowing effect of the SL technique, the resulting fluorescence spectrum of the tissues sample becomes better resolved with a plurality of readily identifiable sharp individual emission peaks.

In many medical applications (e.g., endoscopies), the use of optical fibers is required in order to perform in situ and in vivo measurements in an imaging mode. The inventor has previously disclosed several technologies based on fluorescence and synchronous luminescence for medical applications, such as U.S. Pat. No. 5,599,717 entitled "Advanced Synchronous Luminescence System for Medical Diagnostics," and U.S. Pat. No. 5,938,617 ('617) entitled "Advanced Synchronous Luminescence System for the Detection of Biological Agents and Infectious Pathogens".

'617 teaches a SL system 100 which is shown schematically in FIG. 1. The system 100 includes a laser 102 which provides outputs a light beam 104 having a given wavelength. The light beam 104 is coupled to a structure 106 for changing its wavelength, such as a multi-dye module (MDM) 106. The output of the MDM 106 is delivered, through a focusing lens 108, to a first optical fiber or bundle of fibers 110 for transmitting the excitation radiation to the sample 122 being investigated.

The optical fiber 110 transmits the excitation radiation beam to a probe 120 which is juxtaposed to sample 122. A second optical fiber or bundle of fibers 125 transmits the fluorescence emission from sample 122 to a detector 130. The detector 130 comprises a monochromator (MON) 131 and a photomultiplier (PM) 132. A boxcar integrator (BCI) 134, synchronized with the laser pulse via a pulse generator (PG) 136 acting as a trigger is used to record and process the emitted fluorescence signal. A synchronous scanning device (SS) 138 ensures that the excitation radiation (λex) and the emission radiation (λem) are maintained at a constant interval. A portable computer 140, or other suitable data collection, analysis and/or display devices, can be used to generate a synchronous luminescence spectra which can be compared to spectra from known healthy tissue samples to detect tissue anomalies.

Significantly, system 100 includes a bifurcated fiber probe arrangement where a first probe 110 provides excitation radiation to sample 122 in a first location while a second probe 125 receives emitted radiation from sample 122 from a second sample location. Thus, the excitation and detection locations are different. As a result, co-registration of the excitation and emission is not possible. System 100 also does not generally allow precise determination of the emission location as emissions can originate from a plurality of locations around the excitation location.

SUMMARY OF INVENTION

The invention utilizes the wavelength synchronous scanning method, often referred to as synchronous luminescence (SL), operated in a excitation-detection co-registration imaging mode. The use of excitation-detection co-registration provides increased fluorescent signal levels by providing greater overlap of the excitation and emission focal volumes and improved accuracy in quantitative measurements of signal intensity through use of a single optical path for both the excitation and detection signals. As a result, the invention is expected to provide a significant advance in identification of chemical and biological species and an infectious agents in samples as well as disease; to provide earlier detection of a diseased state (e.g cancer) and aid in the understanding and treatment of disease in general.

A diagnostic method includes the step of exposing at least one sample location with excitation radiation through a single optical waveguide or a single optical waveguide bundle. The sample emits emission radiation in response to the excitation. At least a portion of the emitted radiation is received by the single optical waveguide or single optical waveguide bundle, wherein the single optical waveguide or single optical waveguide bundle provides co-registration of the excitation radiation and emission radiation. The wavelength of the excitation radiation and emission radiation are then synchronously scanned to produce a spectrum. The method can include the step of comparing the spectrum generated to a reference spectrum to identify at least one anomaly in the sample, such as a disease state, a chemical, a biological species or an infectious agent. For example, when the sample is a tissue sample, the method can include the step of determining whether cancer is present in the tissue sample. The method can also include the step of forming an image of the sample.

The excitation radiation can be an intensity-modulated electromagnetic excitation signal, wherein at least one lifetime from the sample can be determined. The intensity-modulated excitation signal can comprise at least one radiation pulse, the radiation pulse having a pulse width shorter than the lifetime, wherein the lifetime is determined using time-resolved spectroscopy. A plurality of periodic radiation pulses can be used.

The intensity-modulated electromagnetic excitation signal can be modulated at a frequency greater than a reciprocal of said sample lifetime, wherein the lifetime can be determined using phase-resolved spectroscopy. The synchronously scanning step can comprise maintaining a constant interval between the wavelength of the excitation radiation and a wavelength of the emission radiation while the excitation and emission wavelengths are scanned. Alternatively, the synchronous scanning mode can be set such that the value of the emission wavelength is a specific function of the value of the excitation wavelength during scanning, the specific function being a non-constant interval between the wavelength of the excitation radiation and the wavelength of the emission radiation. This arrangement can in certain situations improve spectral resolution. For example, the emission wavelength can be a constant other than 1 (e.g. 1.7) multiplied by the excitation wavelength, or a non-linear function of the emission wavelength.

The synchronous scanning step can comprise directing broadband excitation radiation into a first acousto-optic tunable filter (AOTF), and varying an input radio frequency to the first filter to achieve a range of wavelengths of the excitation radiation. The step of scanning a wavelength of said excitation radiation can include directing the excitation radiation to a first AOTF and applying a radio frequency signal to the first AOTF to achieve a range excitation wavelengths. The step of scanning a wavelength of the emission radiation can include directing the emission radiation to a second AOTF and applying a radio frequency signal to the second AOTF to achieve a range of emission wavelengths. A constant interval ($\Delta\lambda$) between the wavelength of the excitation radiation and emission radiation can be maintained during the synchronous scanning step. Alternatively, the synchronous scanning mode can be set such that the value of the emission wavelength is a specific function of the value of the excitation wavelength, rather than a constant interval ($\Delta\lambda$) apart.

A system for testing samples includes an excitation radiation source for generating excitation radiation, a single optical waveguide or a single optical waveguide bundle for transmitting said excitation radiation to at least one sample location, the sample emitting emission radiation in response to the excitation radiation. The emitted radiation signal is received by the single optical waveguide or a single optical waveguide bundle, wherein co-registration of the excitation radiation and emission radiation is provided. The system includes structure for synchronously scanning a wavelength of the excitation radiation and the wavelength of the emission radiation to produce a spectrum. A constant interval between the wavelength of the excitation radiation and the wavelength of the emission radiation can be maintained during the synchronous scanning.

The system can include structure for modulating the excitation radiation to produce intensity-modulated excitation radiation and signal processing circuitry for receiving the emission radiation and for determining spectroscopic data including at least one lifetime of the sample. The intensity-modulated excitation radiation can comprise one or more radiation pulses, the radiation pulses having a pulse width shorter than the lifetime, wherein the lifetime is determined by signal processing circuitry using time resolved spectroscopy.

The excitation radiation source can be a broadband source, wherein the structure for synchronously scanning comprises a first AOTF having a variable input radio frequency selected to achieve a range of excitation wavelengths. The structure for synchronously scanning can further comprise a second AOTF having a variable input radio frequency selected to achieve a range of emission wavelengths.

The system can include a detector for imaging the emitted radiation signal. The detector can be an intensified charge-coupled device (ICCD). A control system can be provided for synchronizing the excitation radiation with detection of the emission radiation by the detector.

BRIEF DESCRIPTION OF THE DRAWINGS

A fuller understanding of the present invention and the features and benefits thereof will be accomplished upon review of the following detailed description together with the accompanying drawings, in which:

FIGS. 2A and 2B show the operation of an acousto-optic tunable filter (AOTF).

DETAILED DESCRIPTION OF THE PREFERRED EMBODIMENTS

Figure 1:
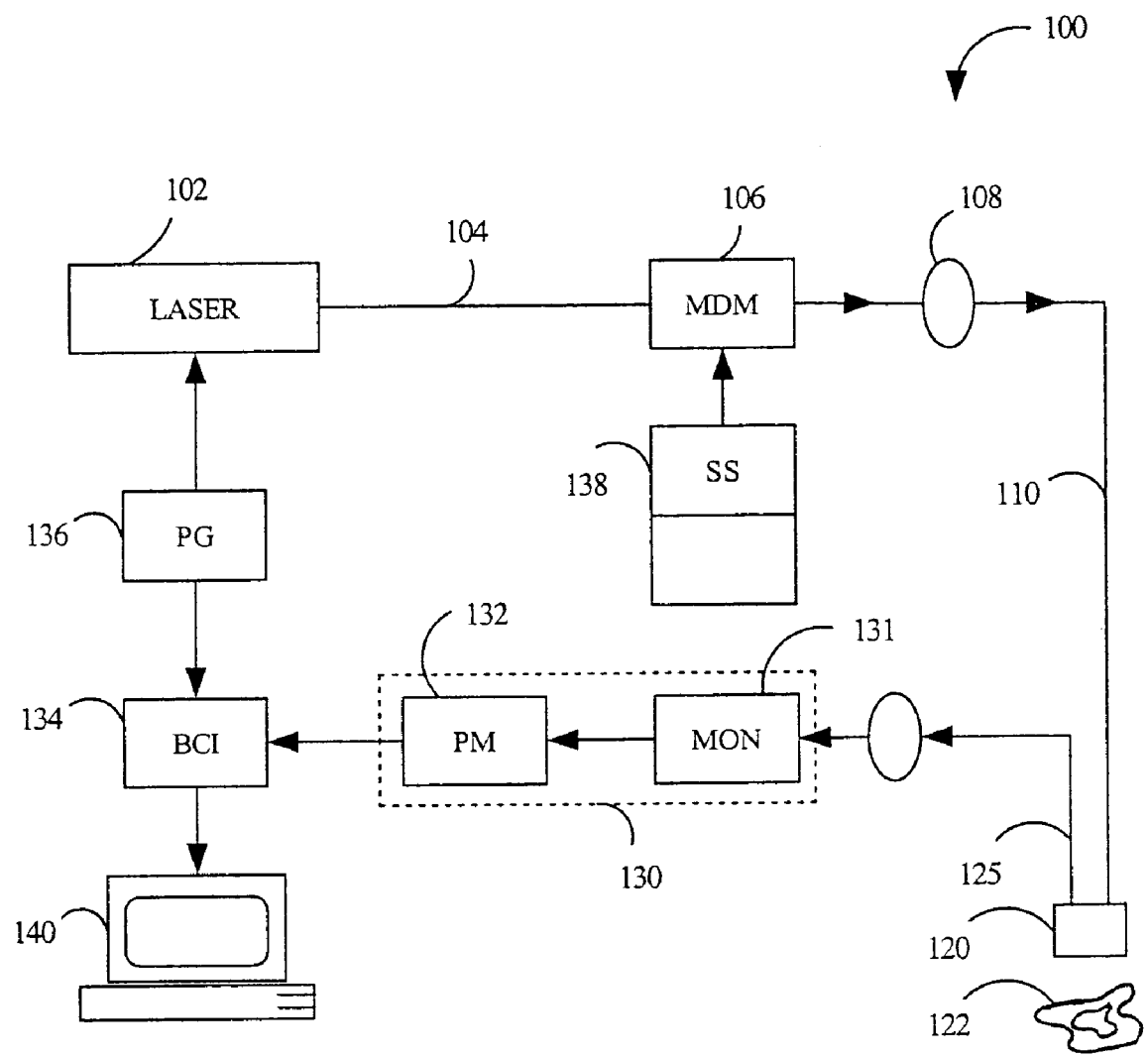
FIG. 1 illustrates a prior art synchronous luminescence (SL) system which includes a bifurcated probe, where separate probes are used to transmit the excitation radiation and to receive the emission radiation, respectively.

The invention includes methods and systems for chemical and medical diagnostic imaging which utilize synchronous luminescence where the wavelength of the excitation radiation and the wavelength of the emission radiation is synchronously scanned to produce a multi-spectral image. The invention operates in an excitation-detection co-registration (EDC) imaging mode, where the emission is taken from the same sample location that is excited.

Co-registration is preferably provided by a single optical waveguide, such as an optical fiber, or a single imaging fiber bundle, rather than the bifurcated fiber probe arrangement disclosed in the '617 patent which includes a first probe (or probe bundle) for providing excitation radiation to a first location of a sample and a second probe (or probe bundle) for receiving emitted radiation from a second location of the sample. Thus, the invention combines the SL technique with spectral imaging based on the EDC approach and renders spectroscopic information obtained in image form. In principle, almost any spectroscopic method, such as scattering including Raman scattering, and emissions including fluorescence and phosphorescence can combined with imaging according to the invention. As used herein, the term "emission" includes not only the process of fluorescence and phosphorescence, but also includes the process of Raman scattering. These techniques can include computer-based digital image processing.

With conventional imaging, the optical emission from every pixel of an image can be recorded, but only at a specific wavelength or spectral bandpass. Thus, the signal at every wavelength within a spectral range can be recorded, but for only a single analyte spot. On the other hand, multi-spectral imaging (MSI) combines these two recording modalities and allows recording the entire emission for every pixel on the entire image in the field of view with the use of a rapid-scanning solid-state device, such as an acousto-optic tunable filter (AOTF) or liquid crystal tunable filter (LCTF).

MSI allows effective excitation of samples (e.g., tissue) with an appropriate wavelength of light and permits collection of two-dimensional (2-D) spectroscopic images across the surface of samples. Spectroscopic analysis of the 2-D images may provide important information that assists in detecting dysplasia and early cancer without the need for extensive pinch biopsies, which involve physical removal of tissues for laboratory analyses.

Due to the simplifying nature of SL, the accuracy of in-vivo dysplasia diagnosis can be dramatically improved. Such a diagnosis technique coupled with MSI imaging technology can provide a minimally invasive analysis that allows for nearly instant diagnosis of tumors without biopsy, thereby allowing for earlier treatment.

The invention preferably uses a scanning device to permit MSI imaging. For example, AOTF technology may be used. An AOTF is non-scanning solid-state device based on an electronically tunable optical bandpass filter. AOTFs offer several advantages over conventional monochromators. An AOTF is an electro-optic device that is used to select and transmit a single wavelength of light from a broadband (e.g. white) light source. Unlike a tunable grating monochromator, an AOTF is a compact solid-state device, which has no moving mechanical parts, and an AOTF can be tuned to any wavelength within its operating range in microseconds. In addition, AOTFs, which are not limited by the small slit size associated with dispersive devices, can increase the light intensity throughout the detection. These characteristics, combined with the small size of these devices, make AOTFs an important new alternative to conventional monochromators, especially for portable instrumentation in field applications.

In AOTFs a piezoelectric transducer is bonded to a birefringent crystal (typically $TeO_2$ or quartz). The transducer is excited by a radio frequency (RF) signal at 50–200 MHz and generates acoustic waves in a birefringent crystal. Those waves temporarily establish a periodic modulation of the index of refraction of the crystal via the elasto-optic effect. Under proper conditions, the AOTF will diffract part of the incident light within a narrow frequency range. This is the basis of an electronically tuned optical filter using the Bragg diffraction of light by periodic modulations in the index of refraction in the crystal established by the acoustic waves. Only light within a narrow frequency range is diffracted by this "phase grating." Only light that enters the crystal such that its angle to the normal of the face of the crystal is within a certain range can be diffracted by the Bragg grating. This range is called the acceptance angle of the AOTF.

As shown in FIG. 2A, the Bragg grating (not shown) within the non-colinear AOTF crystal 210 causes excitation light 215 having the wavelength of interest ($\Delta_D$) to be diffracted off at a slight angle (θ of about 6 degrees) as diffracted light 220 and 225 from the rest of the transmitted light 230 which is not diffracted. The percentage of light diffracted is the diffraction efficiency of the device. This parameter greatly depends on the incidence angle of excitation light 215, the wavelength selected and the power of the RF signal from the transducer which is applied to the crystal.

The AOTF crystal is commonly cut and aligned in a housing device such that the diffracted beam 260 appears to come out from the housing 270 which includes the AOTF in a direction which is parallel with respect to the excitation beam 255 whereas the non-diffracted beam 275 emerges from housing 270 in a direction forming an angle (θ of about 6 degrees) with respect to the excitation beam as shown in FIG. 2B. This design facilitates optical alignment of the AOTF.

As an alternate to an AOTF, liquid crystal tunable filters (LCTF) can be used. Through adjustment of a retarding element of the LCTF a selectable range of excitation wavelengths can be passed. However, AOTFs are generally preferred over LCTFs due to considerations such as convenience and size.

Figure 3:
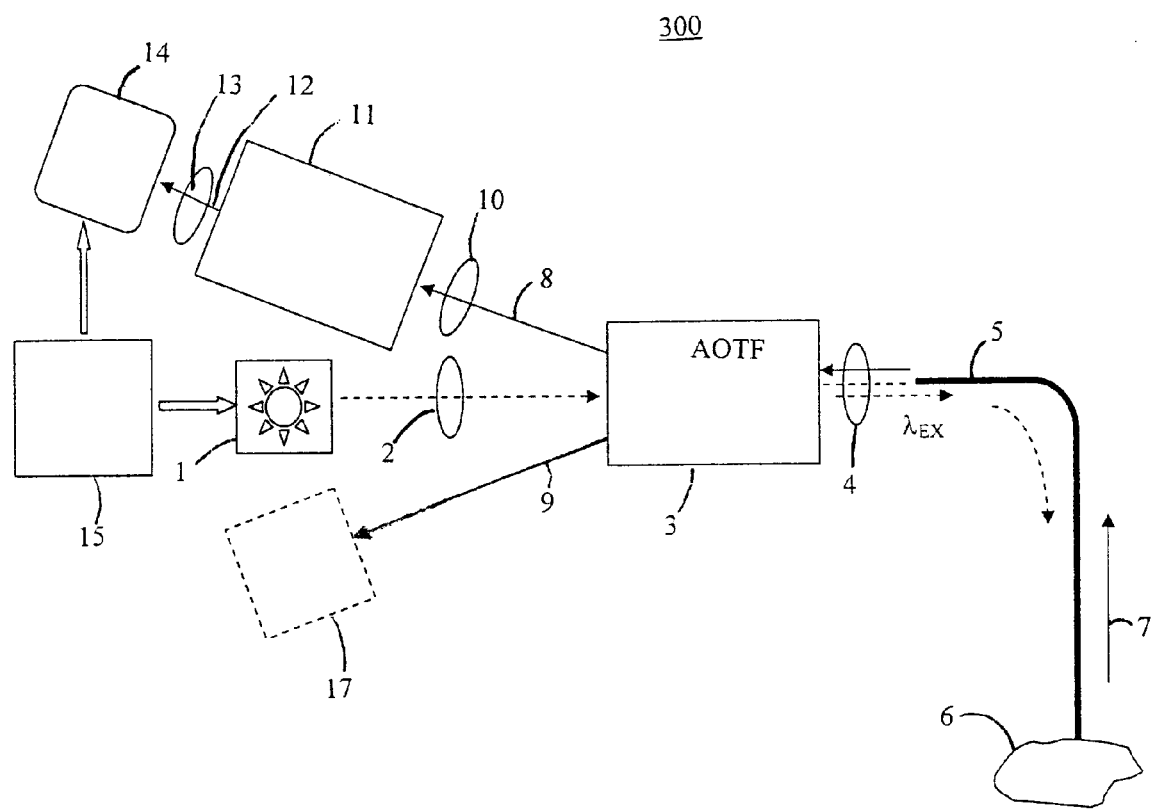
FIG. 3 illustrates the schematic of an exemplary excitation-detection co-registration synchronous luminescence (EDC-SL) system, according to an embodiment of the invention.

An exemplary EDC-SL system 300 according the invention is shown in FIG. 3. A broadband light source, such as from a xenon light source 1 is launched via optics 2 (optional) into the first AOTF device 3 in order to select the desired monochromatic excitation light beam $\lambda_{EX}$. For example, a xenon flashlamp (Oriel Corp., Stratford Conn.; 5–25 kW) could be used to provide the excitation source 1. Xenon lamps provide an intense broadband emission over the visible region of the electromagnetic spectrum, which together with an AOTF provide a single light source capable of producing the continuum of wavelengths desired for excitation of various tissue components. The monochromatic light at wavelength $\lambda_{EX}$, which comes out straight from the AOTF device housing 3 is launched via appropriate optics/lens system 4 (optional) into an optical fiber (or fiber bundle) 5. The fiber 5 can be an imaging fiberscope (Olympus, 2T-10). This excitation light excites the sample 6 on the other end of the fiberscope 5.

The emission signal 7 emanated from the sample 6 is transmitted back through the optical fiber 5 and launched back to AOTF device 3. The zero-order undiffracted light comes out from AOTF device 3 at a light path tilted at approximately 6 degrees. This undiffracted emission light consists of two beams 8 and 9 (optional) which contains all the emission light from the sample, except the excitation light at $\lambda_{EX}$ that comes out straight from AOTF 3. The undiffracted emission beam 8 is then launched via optics 10 into the second AOTF device 11 that is used to select the emission wavelength $\lambda_{EM}$. The diffracted beam 12 at selected wavelength $\lambda_{EM}$ is focused via optics 13 into detector 14. The detector is preferably an intensified charge-coupled device (ICCD, Princeton Instruments), which is a charge-coupled device equipped with an intensifier. The intensifier device allows the detector 14 to be accurately turned on and off (gated) in time intervals of less than about 5 ns.

A control system 15 (optional) can be used to synchronize the light source 1 excitation cycle with the detection cycle, if desired. The other undiffracted emission beam 9 can optionally be used by an operator to look at the sample image on a TV monitor 17 or an eyepiece (not shown).

RF generators (e.g. Brimrose Model AT; not shown) provide RF power (0–25 W) to the respective AOTF crystals. The Brimrose Model AT RF system can be operated using a DOS-based computer having a 16-bit computer controller board supplied by Brimrose. To control the AOTF system, custom-based software has been developed, however any suitable software will suffice. The software programs are designed to run various scanning modes and fixed frequency operation.

The resolution of the AOTFs should be carefully selected for SL measurements. With the SL technique, both $\lambda_{EM}$ and $\lambda_{EX}$ are scanned synchronously with a preferably constant interval $\Delta\lambda$ between the two wavelengths ($\Delta\lambda=\lambda_{EM}-\lambda_{EX}$). To avoid overlap between excitation and emission light, it is important that the $\Delta\lambda$ value be at least twice the selected spectral bandwidth of the AOTF. For example, if $\Delta\lambda$ is selected to be 6 nm, then the AOTF bandwidth must generally be less than 3 nm.

Another AOTF criterion is the minimum resolution for the emission spectra. This resolution is selected in order to match the bandwidth of the fluorescence (or other emission) spectra at room temperature. At room temperature, luminescence spectra of organic compounds exhibit a spectral bandwidth of generally about 15–30 nm. Therefore, a 6 or 10 nm spectral resolution is sufficient to record these spectra and also is large enough to collect sufficient radiation energy in order to decrease the overall monitoring time. The 6 or 10 nm resolution should allow sufficient separation of the various fluorophores when using synchronous luminescence. Furthermore, the selected bandwidths of the AOTFs also match the broad absorption bands of the fluorophores, thus increasing the amount of energy absorbed by the species in the sample, thus resulting in a more intense fluorescence signal.

Figure 4:
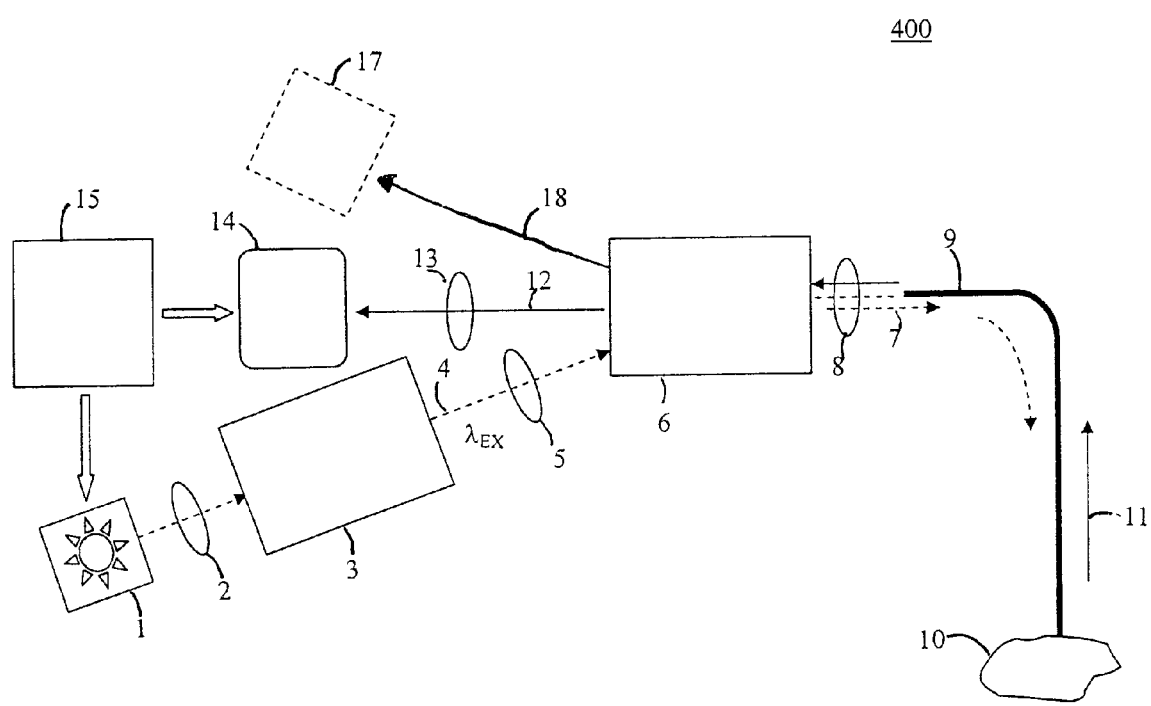
FIG. 4 illustrates the schematic of an exemplary excitation-detection co-registration synchronous luminescence (EDC-SL) system, the system including an intensified charge-coupled device (ICCD) for detection, according to an embodiment of the invention.

An alternate EDC-SL system embodiment 400 is shown in FIG. 4. Light from broadband light source 1 is transmitted via appropriate optics 2 through the first AOTF device 3 that selects the desired excitation wavelength $\lambda_{EX}$. This monochromatic excitation beam 4 having wavelength $\lambda_{EX}$ is then launched via optics 5 into the second AOTF device 6 at an angle of approximately 6 degrees with respect to the normal direction of the crystal. Due to the special geometrical alignment of the AOTF crystal discussed relative to FIG. 2B, the non-diffracted excitation light beam $\lambda_{EX}$ comes out normal to the second AOTF device 6. Therefore the light beam ($\lambda_{EX}$) behaves like non-diffracted zero-order light in the second AOTF device 6 and comes out normal to the aperture plane of the AOTF. The light is then focused via optics 8 onto the imaging fiber or bundle of fibers of the fiberscope 9 (e.g. Olympus, 2T-10) to excite the sample 10.

The emission light 11 from the sample 10 is transmitted through the imaging fiberscope 9 into the second AOTF device 6, which is used to select the desired emission wavelength ($\lambda_{EM}$) of the luminescence signal. Only the monochromatic light beam 12 at wavelength $\lambda_{EM}$ is transmitted by the AOTF device 6 via optics 13 on to the detector 14. The detector 14 is preferably an intensified charge-coupled device (ICCD) which can be accurately turned on and off (gated) in time interval of less than 5 ns. The other undiffracted emission beam 18 can optionally be used by the operator to look at the excitation image through a TV monitor 17 or an eyepiece (not shown).

Although continuous (CW) light sources can be used with the invention, in many applications use of a pulsed excitation light source provides significant advantages. For example, pulse excitation and gated detection allows discrimination (elimination) of the CW (continuous wave) ambient light in the room as well as forward scattered radiation to provide an enhanced signal to noise ratio (SNR) as compared to conventional CW techniques. With a gated detection system having different delays time with respect to a pulsed excitation trigger, it is possible to selectively detect luminescence having a specific lifetime.

Using the invention, optical signals can be measured from a wide variety of spectroscopic processes, including fluorescence, phosphorescence and Raman scattering. One important parameter of the signal emanating from samples of interest is the lifetime of the radiation emanated. The lifetimes of selected various processes are as follows:

(1) absorption: instantaneous with excitation
(2) fluorescence: $10^{-10}$ sec to $10^{-8}$ sec
(3) phosphorescence: $10^{-6}$ to $10^{-3}$ sec
(4) scattering: almost instantaneous with excitation.

In the time-resolved method, a pulsed excitation signal is used. The width of the excitation signal is generally much shorter than the emission or other process of interest, so that the excitation width is much shorter than the lifetime or lifetimes (also referred to as decay time(s)) of the samples. If it is desired to measure the lifetime, the time-dependent emanated intensity I(t) can be measured following the excitation pulse. The decay time ($\tau$) can then be calculated from the slope of a plot of log I(t) versus t, where I is the intensity and t is time, or from the time at which the emanated signal intensity (I) decreases to 1/e (about 37%) of the initial emanated intensity value I(t=0).

Figure 5A:
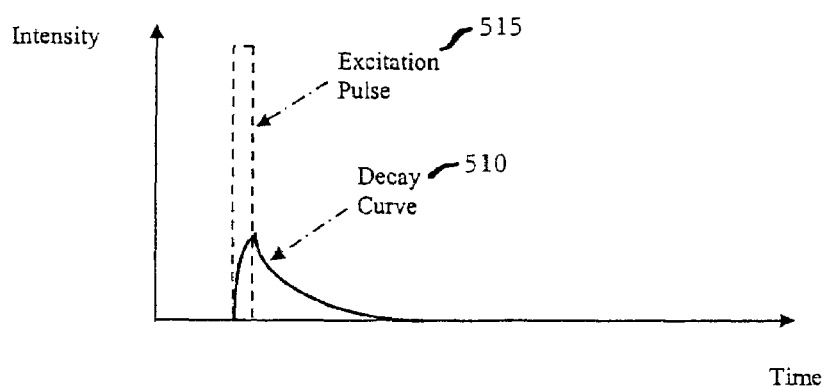
FIG. 5A illustrates an exemplary excitation pulse and the resulting decay curve response.

To measure the emission (or other emanated signal) intensity free from influence from the excitation pulse 515, the detection process can begin after a delay time (dt) sufficiently after the excitation pulse such that the excitation pulse intensity has decreased close to zero as shown in FIG. 5A. In this method, the decay curve 510 represents the detection signal to be analyzed. Different compounds generally provide different characteristic decay time(s). Thus, compounds present in samples can be identified on the basis of their decay times, such as the time to reach 1/e of the initial emanated intensity value at the end of the excitation pulse 515.

Figure 5B:
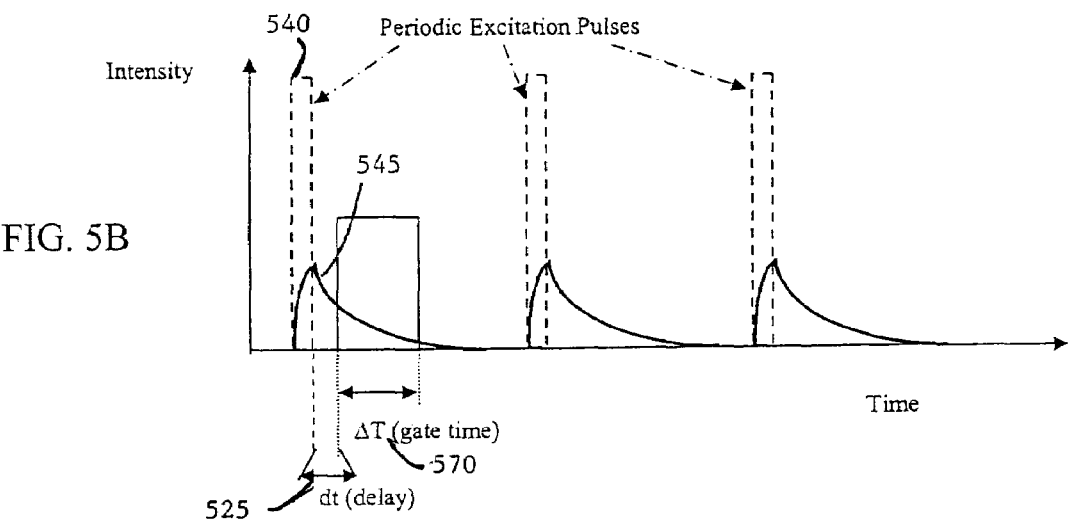
FIG. 5B illustrates a train of periodic excitation pulses and the resulting decay curve responses.

Alternatively, different compounds having different decay times can be differentiated by using different delay times (dT) 525 and gate times ($\Delta T$) 570 as shown in FIG. 5B. The gate time ($\Delta T$) corresponds to the time window (portion) of the decay curve 545 in which detection takes place. For example, the emission of a compound having a short decay time could be detected using a short gate time, while a longer decay time sample would require a longer gate to properly register to provide a good signal-to-noise value. To distinguish between two compounds with only one being present, but not knowing which one, two measurements can be performed using two different (short and long) gate times.

If the measurements using two gate times show the same results (same signal intensities), it could be concluded that the compound with the short decay time is present, as all the short-decay emission fits in the two gate windows. However, if the two gate times produce different results, such as the signal obtained with the short gate time is lower than the signal with the longer gate time, it could be concluded that the compound present was the one having a long gate time. Similar variations could be performed using a fixed gate time and varying the delay time. A long delay time would cause the measurement to miss short-decay emissions, but register long-decay emissions. A short delay time would register both emissions.

In imaging diagnostics, spectral images of an area of interest can be recorded at different gate and delay time conditions. The data obtained can be analyzed using standard mathematical tools for image data analysis.

An important source of noise in many measurement situations is DC noise from the background. Improvement in signal-to-noise can be achieved by using multiple periodic excitation pulses, and by applying the "boxcar" method by integrating the emission signal during a gate time ($\Delta T$) after each excitation pulse 540 as also shown in FIG. 5B.

Another factor that favors pulsed-excitation sources when choosing an excitation source for the in-vivo fluorescence measurements of human tissue is because photobleaching of the fluorophore is often a problem. To help alleviate this problem, a pulsed excitation source used in conjunction with a gated detector could reduce the total illumination time of the sample. By using a high-powered pulsed excitation source, the overall imaging time of the instrument can be reduced greatly. In either of these two designs, an AOTF (Brimrose Corp. Baltimore, Md.) will be used for the selection of the excitation wavelength.

Figure 6:
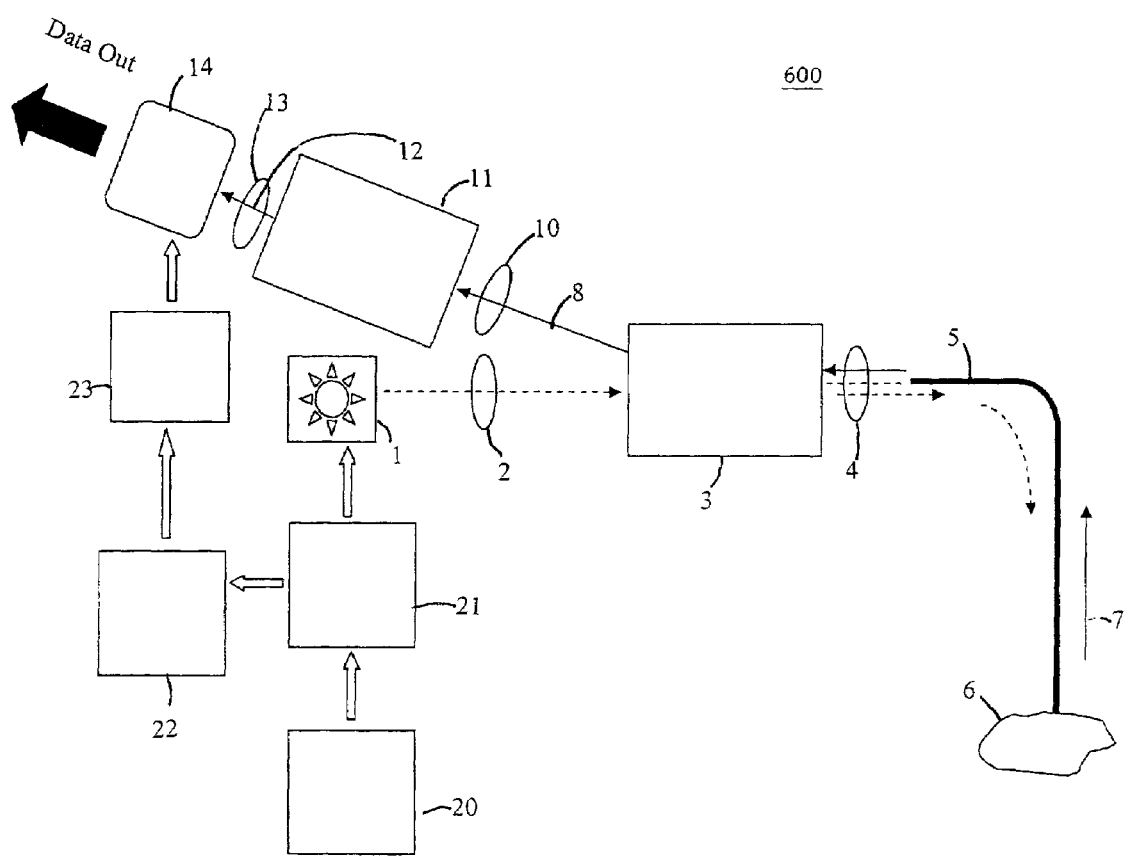
FIG. 6 illustrates an EDC-SL system which provides time-resolved detection, according to another embodiment of the invention.

FIG. 6 shows a system adapted for time-resolved measurements 600, where a frequency generator such as a crystal oscillator 20 is used to select the frequency of the measurements. The frequency generator 20 output is supplied to driver 21, which is used to pulse the output amplitude of a broadband light source 1.

Broadband light source 1, such as from a xenon source, is launched via appropriate optics 2 (optional) into the first AOTF device 3 in order to select the monochromatic excitation light beam $\lambda_{EX}$. The excitation source 1 is a broadband light source. A xenon flashlamp (Oriel Corp., 5–25 kW) could be used to provide such an excitation source. Xenon lamps provide an intense broadband emission over the visible region of the electromagnetic spectrum, thereby providing a single light source capable of producing the continuum of wavelengths desired for excitation of various tissue components. The monochromatic light at wavelength $\lambda_{EX}$, which comes out straight from the AOTF device housing 3, is launched via appropriate optics/lens system 4 (optional) into an optical fiber (or fiber bundle) 5. The fiber can be an imaging fiberscope (Olympus, 2T-10).

This excitation light excites the sample 6 on the other end of the fiberscope 5. The emission or other emanated signal 7 from the sample is transmitted back through the imaging fiber bundle 5 through optics/lens system 4 back onto AOTF device 3. The zero-order undiffracted light comes out from AOTF device 3 at a light path tilted at approximately 6 degrees. This undiffracted emission light consists of two beams 8 and 9 (not shown) contains all the emission light from the sample (except the excitation light at $\lambda_{EX}$ that comes out straight). The emission beam 8 is then launched via optics 10 into the second AOTF device 11 that is used to select the emission wavelength $\lambda_{EM}$. The diffracted beam 12 at selected wavelength $\lambda_{EX}$ is focused via optics 13 into the detector 14. The detector is preferably an intensified charge-coupled device (ICCD, Princeton Instruments).

The driver 21 is synchronized with a delay generator 22. The delay generator 22 is used to open the gating device 23 that operates the intensifier device of ICCD 14. The intensifier device allows the detector to be accurately turned on and off (gated) in time intervals of less than 5 ns.

Figure 7:
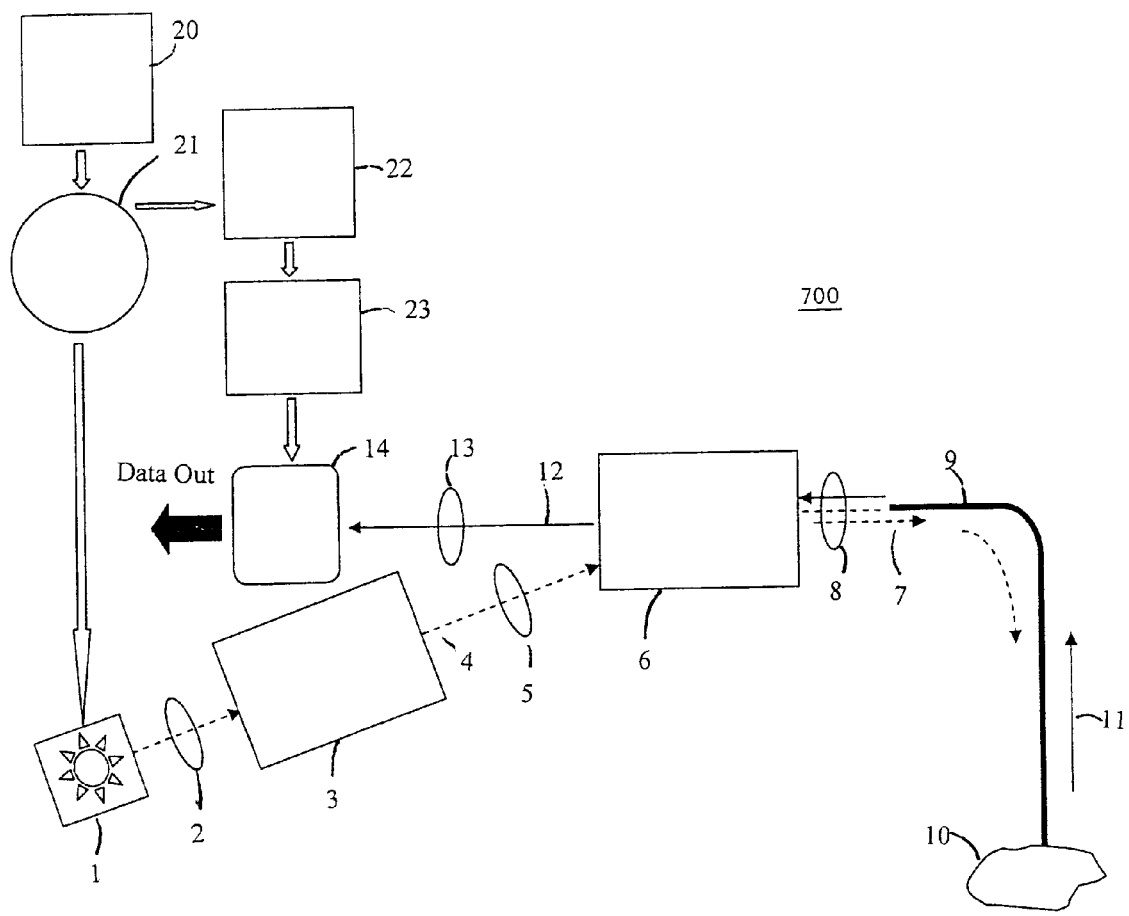
FIG. 7 illustrates an alternate embodiment of an EDC-SL system which provides time-resolved detection, according to an embodiment of the invention.

FIG. 7 shows another embodiment of A time-resolved EDC-SL system 700, where a frequency generator 20, such as a crystal controlled oscillator, is again used to select the frequency of the measurements. The frequency generator operates a driver 21, which is used to pulse the excitation light source 1. Light from the excitation light source 1 is transmitted via appropriate optics 2 through the first AOTF device 3 that selects the desired excitation wavelength $\lambda_{EX}$. This monochromatic excitation beam 4 having wavelength $\lambda_{EX}$ is then launched via optics 5 into the second AOTF device 6 at an angle of approximately 6 degrees with respect to the normal direction. Due to the special geometry alignment of the AOTF crystal discussed above, the non-diffracted excitation light beam $\lambda_{EX}$ comes out normal to the second AOTF device 6. Therefore the light beam ($\lambda_{EX}$) behaves like a non-diffracted zero-order light in the second AOTF device 6 and comes out normal to aperture plane of the AOTF. Then the light focused via optics 8 onto the imaging bundle of the fiberscope 9 to excite sample 10.

The emission (or other emanated) light 11 from the sample 10 is transmitted through the imaging fiberscope 9 into the second AOTF device 6, which is used to select the desired emission wavelength ($\lambda_{EM}$) of the luminescence signal. Only the monochromatic light beam 12 at wavelength $\lambda_{EM}$ is transmitted by the AOTF device 6 and transmitted via optics 13 on to the detector 14. The detector 14 is preferably an intensified charge-coupled device (ICCD).

The driver 21 is synchronized with a delay generator 22. The delay generator is used to open the gating device 23 that operate the intensifier device of ICCD 14 which allows the detector to be accurately turned on and off (gated) in time interval of preferably less than about 5 ns.

The four embodiments of the invention described in FIGS. 3, 4, 6 and 7 all provide EDC through a single fiber (or fiber bundle) probe. This results in improved detection of diseases, including improved quantitative measures. The EDC scheme also provides an increased fluorescence (or other emanated) signal by producing a greater overlap of the excitation and emission focal volumes. This feature increases the sensitivity of the instrument as well as decreases the exposure time necessary to obtain an image. Furthermore, co-registration allows diagnostics of the same precise surface or volume of a sample or tissue irradiated by the excitation light beam.

It is noteworthy that the imaging fiber or fiber bundle probes shown in FIGS. 3, 4, 6 and 7 are useful for endoscopic examinations because these probes can be inserted into an endoscope or for situations where remote sensing using fibers is desired. For applications relating to measurement surfaces that do not require endoscopic systems or remote fiber probes, the optical fiber can be omitted.

Phase-sensitive detection is another method that can be used to determine lifetimes other than the time-resolved method described above. Instead of using the ICCD as the detector, other detectors are generally used to facilitate phase-sensitive detection. Phase-resolved techniques are often referred to as frequency domain techniques. In the phase-resolved technique, the sample is excited with intensity-modulated light. However, rather than a series of short pulses generally used in the time-resolved method, the intensity of the incident light changes with a single very high frequency ($\omega=2\pi f$, f being the frequency in hertz) as compared to the reciprocal of the target decay time(s) $\tau$ in the sample.

Following excitation with the high-frequency modulation signal, the emission or other signal emanation becomes intensity-modulated at the same modulation frequency. However, since the emission or other emanation follows a decay time, there is a certain delay in the emission relative to the excitation. This delay is generally measured as a phase-shift ($\phi$), which can be used to calculate the decay time. At each modulation frequency $\bar{\omega}$, the delay is described as a phase shift $\phi_\omega$, which increases from 0° to 90° with increasing modulation frequency $\bar{\omega}$.

The finite time response of targets in the sample also results in demodulation of the emission by a factor $m_\omega$. This factor decreases from 1.0 to 0 with increasing modulation frequency. At low frequencies, the emission or other signals emanated closely follow the excitation signal. Accordingly, the phase angle is near zero and the modulation is near 1. As the modulation frequency is increased, the finite lifetime of the emission or other emanation process prevents the emission from closely following the excitation. This results in a phase delay of the emission, and a decrease in the peak-to-peak amplitude of the modulated emission or other signal emanated.

The shape of the frequency response is determined by the number of decay times displayed by the sample. If the decay is a single exponential, the frequency analysis is simplified. In this case, the phase angle or modulation at any frequency can be used to calculate the lifetime. For single-exponential decay, the phase and modulation are related to the decay time ($\tau$) by the following relations:

$$\tan \phi_\omega = \bar{\omega}\tau; \text{ and } m_\omega = (1+\omega^2\tau^2)^{-1/2}$$

Therefore, one can differentiate and thus identify various emissions or other signal emanations having different decay times by selecting the phase shift ($\phi$) optimized to the decay time ($\tau$) of interest.

Figure 8:
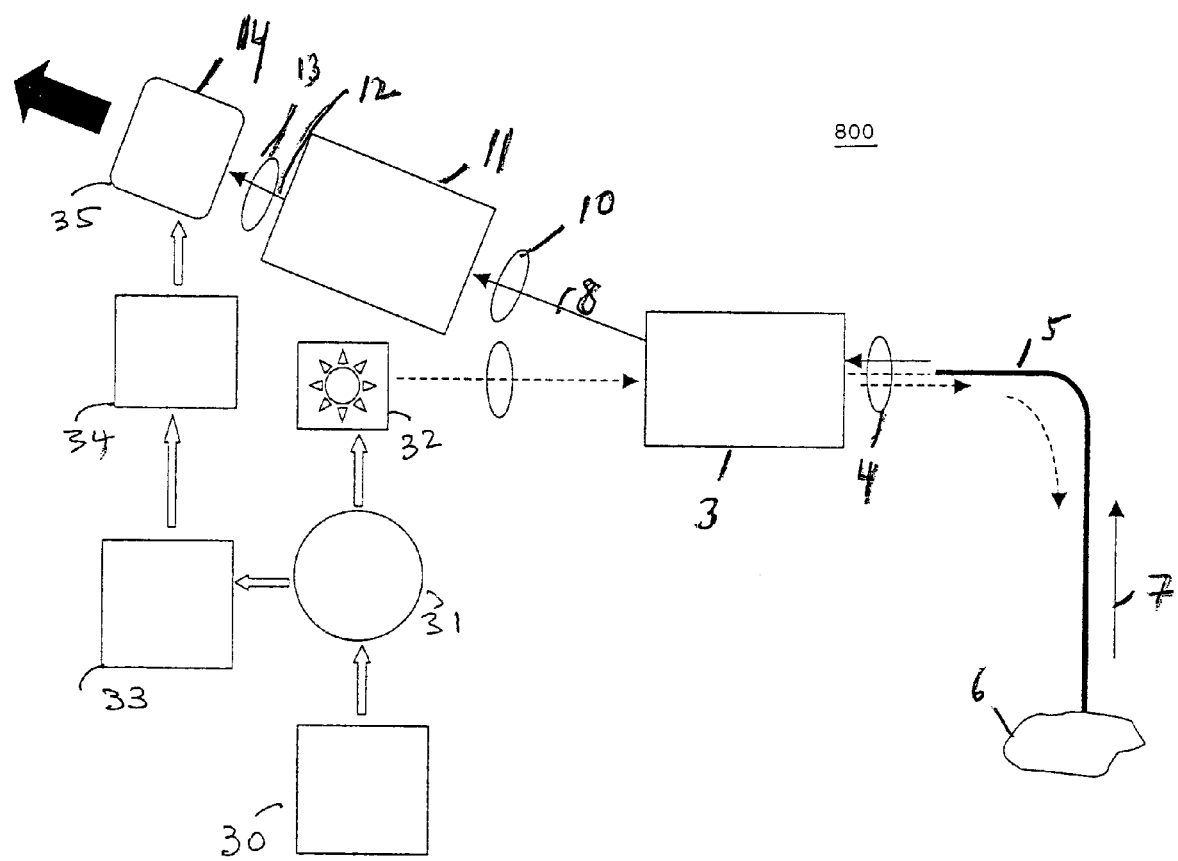
FIG. 8 illustrates an EDC-SL system which provides phase-sensitive detection, according to an embodiment of the invention.

FIG. 8 shows a first embodiment of a system 800 adapted for phase-sensitive EDC-SL measurements. Frequency selector device 30, such as a crystal oscillator, is connected to a modulator 31, which modulates the light source 32. The modulated monochromatic light at wavelength $\lambda_{EX}$, which comes out straight from the AOTF device housing 3, is launched via appropriate optics/lens system 4 (optional) into an optical fiber (or fiber bundle) 5. The fiber 5 can be an imaging fiberscope (Olympus, 2T-10). This excitation light excites the sample 6 on the other end of the fiberscope 5 which produces an emission signal 7.

The emission signal 7 is transmitted back through the optical fiber 5 and launched back to AOTF device 3. The zero-order undiffracted light comes out from AOTF device 3 at a light path tilted at approximately 6 degrees. This undiffracted emission light consists of two beams 8 and 9 (not shown) which contains all the emission light from the sample, except the excitation light at $\lambda_{EX}$ that comes out straight. The undiffracted emission beam 8 is then launched via optics 10 into the second AOTF device 11 that is used to select the emission wavelength $\lambda_{EM}$ The diffracted beam 12 at selected wavelength $\lambda_{EM}$ is focused via optics 13 into the detector 14. The modulator 31 is synchronize with a phase-shift selector 33, which is connected to the phase-sensitive device 34. Phase-sensitive device 34 is connected to the gain-modulated intensifier stage (not shown) of detector 35.

Figure 9:
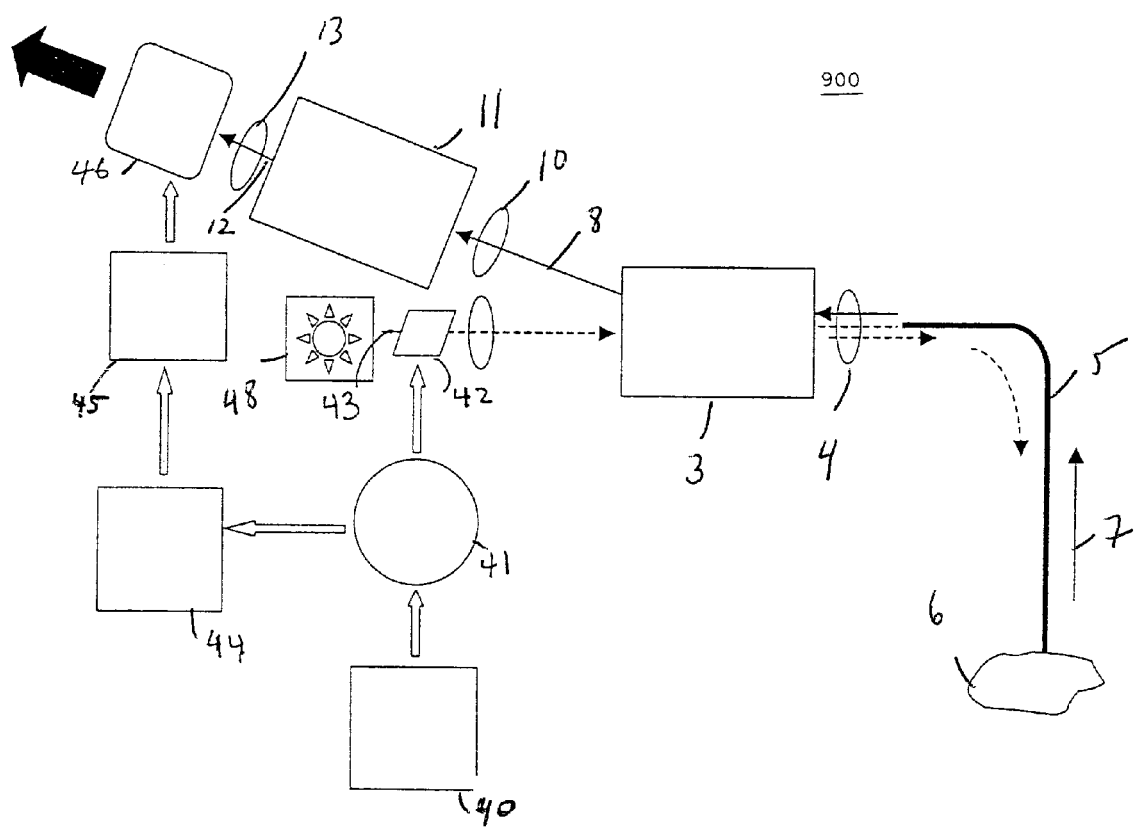
FIG. 9 illustrates an alternate embodiment of an EDC-SL system which provides phase-sensitive detection, according to an embodiment of the invention.

FIG. 9 shows a second embodiment of an EDC-SL system 900 adapted for phase-sensitive measurements. Frequency selector device 40 is connected to a modulator 41, which operates an electro-optic modulator 42, which modulates the light beam 43 provided by excitation light source 48. The modulated monochromatic light at wavelength $\lambda_{EX}$, which comes out straight from the AOTF device housing 3, is launched via appropriate optics/lens system 4 (optional) into an optical fiber (or fiber bundle) 5. The fiber 5 can be an imaging fiberscope (Olympus, 2T-10). This excitation light excites the sample 6 on the other end of the fiberscope 5.

The emission signal 7 from sample 6 is transmitted back through the optical fiber 5 and launched back to AOTF device 3. The zero-order undiffracted light comes out from AOTF device 3 at a light path tilted at approximately 6 degrees. This undiffracted emission light consists of two beams 8 and 9 (not shown) which contains all the emission light from the sample, except the excitation light at $\lambda_{EX}$ that comes out straight. The undiffracted emission beam 8 is then launched via optics 10 into the second AOTF device 11 that is used to select the emission wavelength $\lambda_{EM}$. The diffracted beam 12 at selected wavelength $\lambda_{EM}$ is focused via optics 13 into the detector 46. The modulator 41 is synchronized with a phase-shift selector 44, which is connected to the phase-sensitive device 45. phase-sensitive device 45 is connected to the gain-modulated intensifier stage (not shown) of detector 46.

Figure 10:
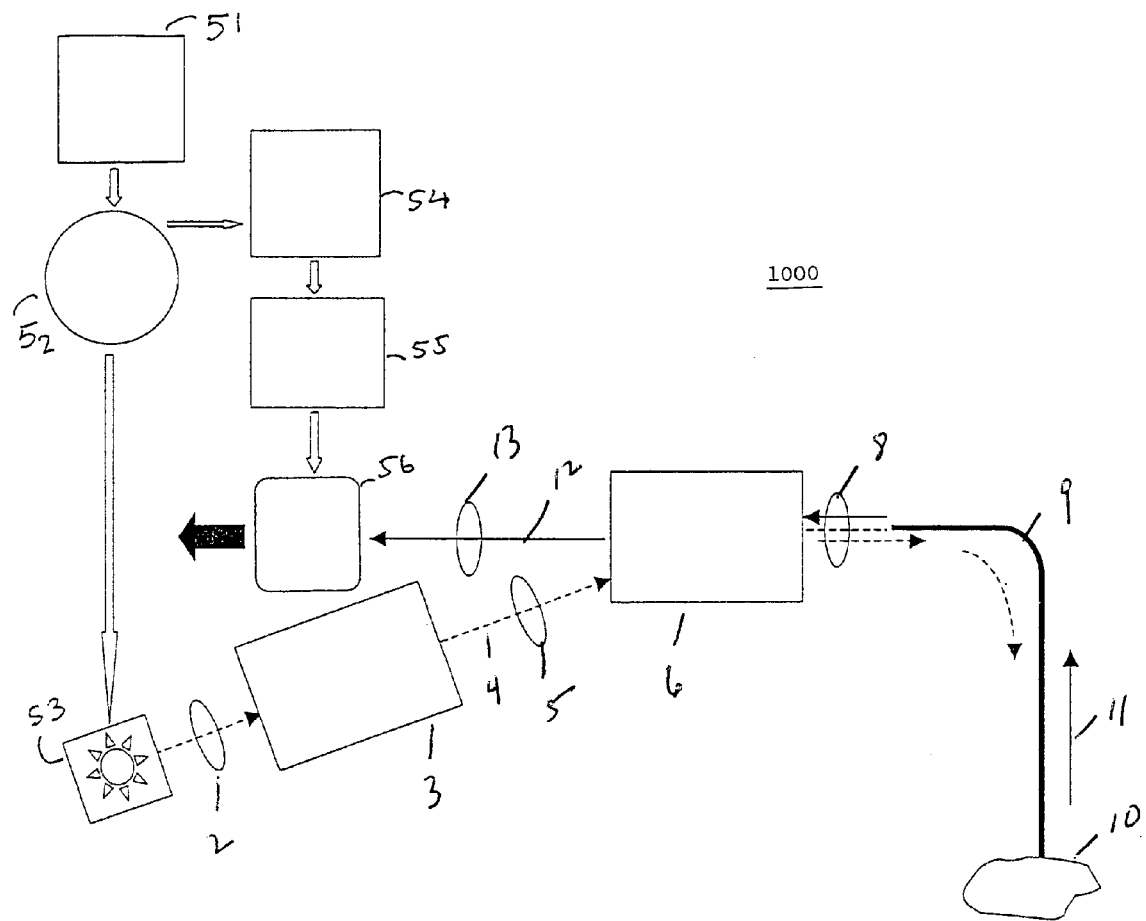
FIG. 10 illustrates another embodiment of an EDC-SL system which provides phase-sensitive detection, according to an embodiment of the invention.

FIG. 10 shows another embodiment of an EDC-SL system 1000 adapted for phase-sensitive measurements. Frequency selector device 51 is connected to a modulator 52, which modulates the excitation light source 53. Light from light source 53 is transmitted via appropriate optics 2 through the first AOTF device 3 that selects the desired excitation wavelength $\lambda_{EX}$. This monochromatic excitation beam 4 having wavelength $\lambda_{EX}$ is then launched via optics 5 into the second AOTF device 6 at an angle of approximately 6 degrees with respect to the normal direction. Due to the special geometry alignment of the AOTF crystal discussed relative to FIG. 2B, the non-diffracted excitation light beam $\lambda_{EX}$ comes out normal to the second AOTF device 6. Therefore the light beam ($\lambda_{EX}$) behaves like a non-diffracted zero-order light in the second AOTF device 6 and come out normal to the aperture plane of the AOTF. The light is then focused via optics 8 onto the imaging fiber or bundle of fibers of the fiberscope 9 (e.g. Olympus, 2T-10) to excite the sample 10.

The emission light 11 from the sample 10 is transmitted through the imaging fiberscope 9 into the second AOTF device 6, which is used to select the desired emission wavelength ($\lambda_{EM}$) of the luminescence signal. Only the monochromatic light beam 12 at wavelength $\lambda_{EM}$ is transmitted by the AOTF device 6 via optics 13 to detector 56. The modulator 52 is synchronized with a phase-shift selector 54, which is connected to the phase-sensitive device 55. Phase-sensitive device 55 is connected to the gain-modulated intensifier stage (not shown) of detector 56.

Figure 11:
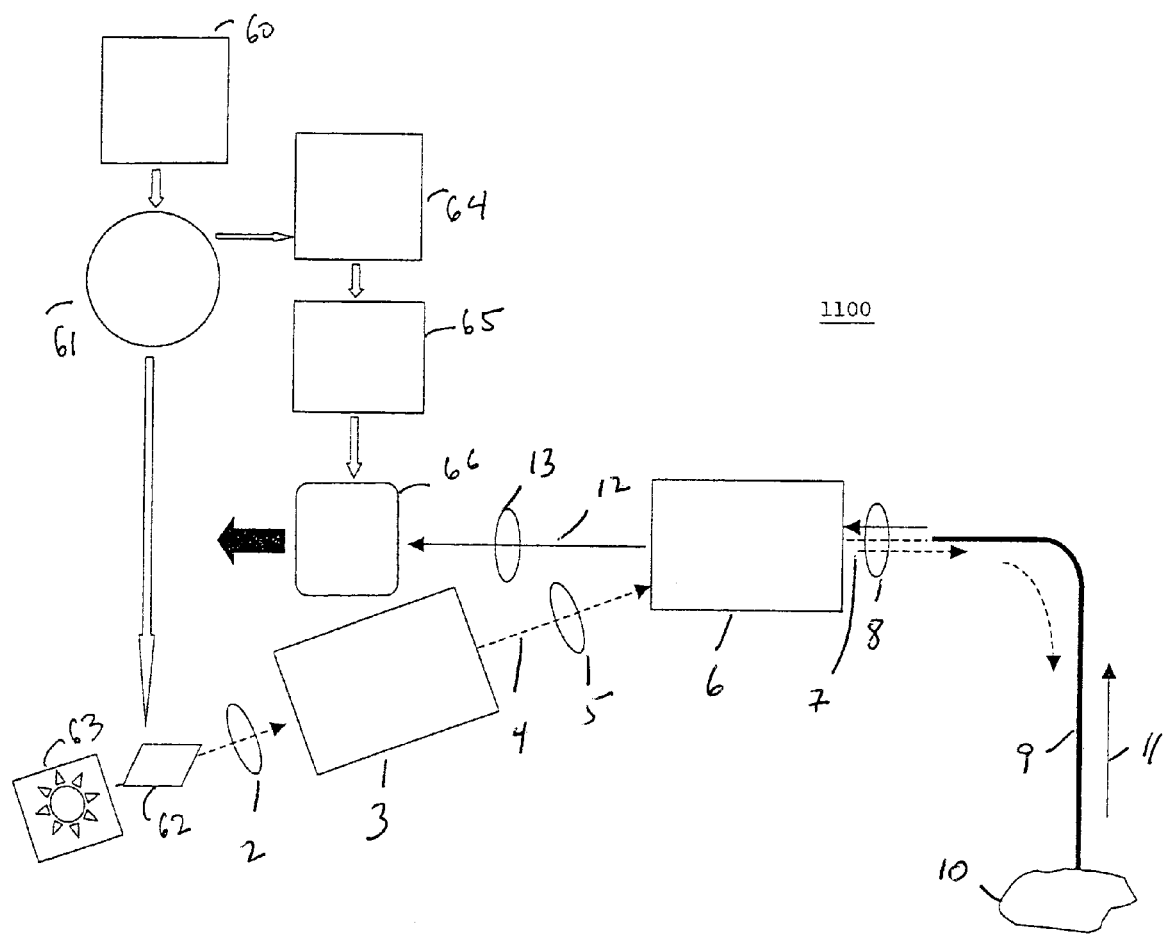
FIG. 11 illustrates yet another embodiment of an EDC-SL system which provides phase-sensitive detection, according to an embodiment of the invention.

FIG. 11 shows yet another embodiment of an EDC-SL system 1100 adapted for phase-sensitive measurements. Frequency selector device 60 is connected to a modulator 61, which operates an electro-optic modulator 62, which modulates light provided by excitation light source 63. Light from light source 63 is transmitted via appropriate optics 2 through the first AOTF device 3 that selects the desired excitation wavelength $\lambda_{EX}$. This monochromatic excitation beam 4 having wavelength $\lambda_{EX}$ is then launched via optics 5 into the second AOTF device 6 at an angle of approximately 6 degrees with respect to the normal direction. Due to the special geometry alignment of the AOTF crystal discussed relative to FIG. 2B, the non-diffracted excitation light beam $\lambda_{EX}$ comes out normal to the second AOTF device 6. Therefore the light beam ($\lambda_{EX}$) 7 behaves like a non-diffracted zero-order light in the second AOTF device 6 and come out normal to the aperture plane of the AOTF. The light 7 is then focused via optics 8 onto the imaging fiber or bundle of fibers of the fiberscope 9 (e.g. Olympus, 2T-10) to excite the sample 10.

The emission light 11 from the sample 10 is transmitted through the imaging fiberscope 9 into the second AOTF device 6, which is used to select the desired emission wavelength ($\lambda_{EM}$) of the luminescence signal. Only the monochromatic light beam 12 at wavelength $\lambda_{EM}$ is transmitted by the AOTF device 6 via optics 13 to detector 66. The modulator 61 is synchronized with a phase-shift selector 64, which is connected to the phase-sensitive device 65. Phase-sensitive device 65 is connected the gain-modulated intensifier stage (not shown) of detector 66. Other approaches such as homodyne mixing techniques [See E. M. Sevick-Muraca, E. Kuwana, A. Godavarty, J. P. Houston, A. B. Thompson and R. Roy, "Near-infrared fluorescence imaging and spectroscopy in random media and tissues", in Biomedical Photonics Handbook, T. Vo-Dinh, Ed., CRC Press, Boca Raton, pp. 33–1 (2003)] which have been developed for frequency-domain detection can also be used.

The invention provides several advantages over conventional detection systems. An increased fluorescence (or other emanated) signal is generated by the greater overlap of the excitation and emission focal volumes provided by coregistration of the excitation and detection signals. This feature increases the sensitivity of the instrument as well as decreases the exposure time necessary to obtain an image. Improved signal intensity particularly aides in imaging opaque, or highly absorbing samples.

In addition, improved accuracy in quantitative measurements of signal intensity is provided through use of a single excitation-detection fiber path where the emission origination location is known. In comparison, use of separate fibers for providing excitation radiation and receiving emission radiation result in receipt of emissions which can come from several areas around the excitation fiber. In addition, prior systems render the path length of the light inside the samples to often be unknown.

The invention is expected to become widely used in a variety of applications, such as medical diagnostics, environmental monitoring, chemical and biological sensing, industrial control, quality control, pharmaceutical, as well as agricultural and petroleum monitoring.

EXAMPLES

It should be understood that the examples and embodiments described herein are for illustrative purposes only and that various modifications or changes in light thereof will be suggested to persons skilled in the art and are to be included within the spirit and purview of this application. The invention can take other specific forms without departing from the spirit or essential attributes thereof.

Figure 12A:
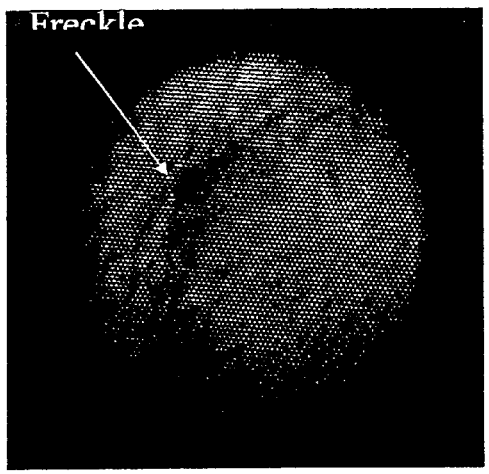
FIG. 12A shows a spectral image of skin surface using excitation at 488 nm while the AOTF was also set at 488 nm, thus recording reflected light in the image, the dark spot shown corresponding to a freckle on the skin.
Figure 12B:
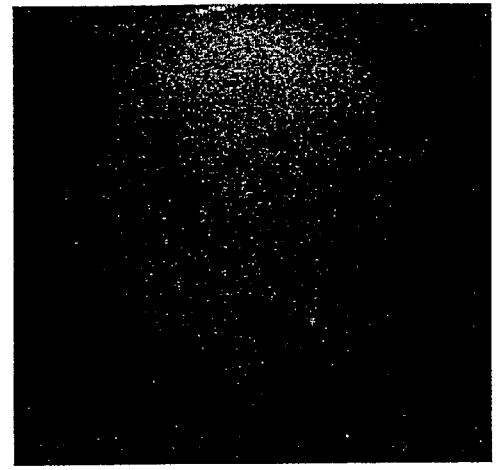
FIG. 12B represents the same skin area shown in FIG. 12A again using excitation at 488 nm. However, the AOTF was scanned to 640 nm to provide a wavelength interval $\Delta\lambda$ between the two wavelengths of 152 nm to record a fluorescence image. The freckle is no longer visible in the fluorescence image.

FIGS. 12A and 12B show examples of reflective and fluorescence imaging results, respectively, obtained from an exemplary AOTF system according to the invention. A subject was provide having a skin surface that included a freckle. The purpose of the demonstration was to determine whether the freckle was cancerous. It is known that cancerous freckles fluoresce differently as compared to non-cancerous freckles and normal skin tissue.

FIG. 12A shows a recording of the spectral image of the skin surface using excitation at 488 nm. The AOTF (Brimrose) wavelength was also set at 488 nm, thus recording the diffuse reflectance light in the image. In this case the wavelength interval ($\Delta\lambda$) between the two wavelengths $\Delta\lambda=\lambda_{em}-\lambda_{ex}=0$ nm. The dark spot corresponds to a freckle on the skin surface.

FIG. 12B represents the same skin surface. However, in this figure the AOTF was scanned to another wavelength, 640 nm. In this case the wavelength interval $\Delta\lambda$ between the emission and excitation wavelengths was: $\Delta\lambda=\lambda_{em}-\lambda_{ex}=640$ nm−488 nm=152 nm. Therefore the spectral image is no longer showing the reflected excitation light but only emitted fluorescence light near 640 nm. Note that the freckle image is no longer visible in the fluorescence image. Thus, the freckle was classified as being non-cancerous. The results shown in FIGS. 12A and 12B thus demonstrate one of the many advantages of biomedical imaging using an AOTF-based imaging system. Specifically, the data shown in FIGS. 12A and B show that an AOTF-based imaging system according to the invention can provide a dual modality diagnostic system including both fluorescence and reflectance from a single device.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. A diagnostic methed, comprising the steps of:
   exposing at least one sample location with excitation radiation through a single optical waveguide or a single optical waveguide bundle, wherein said sample emits emission radiation in response to said excitation radiation;
   receiving at least a portion of said emission radiation from said sample location in said single optical waveguide or said single optical waveguide bundle, wherein said single optical waveguide or said single optical waveguide bundle provides co-registration of said excitation radiation and said emission radiation, and
   generating a spectrum using synchronous luminescence, wherein a wavelength of said emission radiation ($\lambda_{em}$) and a wavelength of said excitation radiation ($\lambda_{ex}$) are simultaneously scanned.

2. The method of claim 1, further comprising the step of comparing said spectrum to a reference spectrum to identify at least one anomaly in said sample.

3. The method of claim 2, wherein said anomaly is selected from the group consisting of a disease stare, a chemical, a biological species and an infectious agent.

4. The method of claim 2, wherein said sample is a tissue sample, further comprising the step of determining the presence of cancer in said tissue sample.

5. The method of claim 1, further comprising the step of forming an image of said sample from said spectrum.

6. The method of claim 1, wherein said excitation radiation is an intensity-modulated electromagnetic excitation signal, further comprising the step of determining at least one lifetime from said sample.

7. The method of claim 6, wherein said intensity-modulated electromagnetic excitation signal comprises at least one radiation pulse, said radiation pulse having a pulse width shorter than said lifetime, wherein said lifetime is determined using time resolved spectroscopy.

8. The method of claim 7, wherein said at least one radiation pulse comprises a plurality of periodic pulses.

9. The method of claim 6, wherein said intensity-modulated electromagnetic excitation signal is modulated at a frequency greater than a reciprocal of said lifetime, wherein said lifetime is determined using phase-resolved spectroscopy.

10. The method of claim 1, wherein said generating step comprises maintaining a constant interval between said wavelength of said excitation radiation and a said wavelength of said emission radiation.

11. The method of claim 1, wherein said generating step comprises directing broadband excitation radiation into a first acousto-optic tunable filter (AOTF), and varying an input radio frequency to said first filter to achieve a range of wavelengths of said excitation radiation.

12. The method of claim 11, wherein said step of scanning a wavelength of said excitation radiation comprises directing said excitation radiation to a first AOTF and applying a radio frequency signal to said first AOTF to achieve a range of said excitation wavelengths.

13. The method according to claim 12, wherein said step of scanning a wavelength of said emission radiation comprises directing said emission radiation to a second AOTF and applying a radio frequency signal to said second AOTF to achieve a range of said emission wavelengths.

14. The method of claim 1, wherein said generating step comprises utilizing a non-constant interval between said wavelength of said excitation radiation and said wavelength of said emission radiation.

15. A system for testing samples, comprising:
   an excitation radiation source for generating excitation radiation;
   a single optical waveguide or a single optical waveguide bundle for transmitting said excitation radiation to at least one sample location, said sample emitting emission radiation in response to said excitation radiation which is received by said single optical waveguide or a single optical waveguide bundle, wherein co-registration of said excitation radiation and said emission radiation is provided, and
   structure for generating a spectrum using synchronous luminescence comprising structure for simultaneously scanning a wavelength of said emission radiation ($\lambda_{em}$) and a wavelength of said excitation radiation ($\lambda_{ex}$).

16. The system of claim 15, further comprising structure for modulating said excitation radiation to produce intensity-modulated excitation radiation.

17. The system of claim 16, further comprising signal processing circuitry for receiving said emission radiation and determining spectroscopic data including at least one lifetime of said sample.

18. The system of claim 17, wherein said intensity-modulated excitation radiation comprises at least one radiation pulse, said radiation pulse having a pulse width shorter than said lifetime, wherein said lifetime is determined by said signal processing Circuitry using time resolved spectroscopy.

19. The system of claim 18, wherein said at least one radiation pulse comprises a plurality of periodic pulses.

20. The system of claim 17, wherein said intensity-modulated excitation radiation has a frequency greater than a reciprocal of said lifetime, wherein said lifetime is determined by said signal processing circuitry using phase-resolved spectroscopy.

21. The system of claim 15, wherein said excitation radiation source is a broadband source, structure for synchronously scanning comprising a first acousto-optic tunable filter (AOTF) having a variable input radio frequency selected to achieve a range of excitation wavelengths.

22. The system of claim 21, wherein said structure for generating a spectrum using synchronous luminescence further comprises a second acousto-optic tunable filter (AOTF) having a variable input radio frequency selected to achieve a range of emission wavelengths.

23. The system of claim 15, further comprising a detector for imaging said emission radiation.

24. The system of claim 23, wherein said detector is an intensified charge-coupled device (ICCD).

25. The system of claim 24, further comprising a control system for synchronizing said excitation radiation with detection of said emission radiation by said detector.

* * * * *